(12) United States Patent
Heuer et al.

(10) Patent No.: US 10,441,263 B2
(45) Date of Patent: Oct. 15, 2019

(54) DEVICE FOR CARRYING OUT A DISTRACTION FOR A COMPRESSION OF VERTEBRAL BODIES DURING A SPINAL SURGERY

(71) Applicant: SILONY MEDICAL INTERNATIONAL AG, Frauenfeld (CH)

(72) Inventors: Frank Heuer, Filderstadt (DE); Timo Ohnmacht, Trichtingen (DE)

(73) Assignee: Silony Medical International AG, Frauenfeld (CH)

( * ) Notice: Subject to any disclaimer, the term of this patent is extended or adjusted under 35 U.S.C. 154(b) by 159 days.

(21) Appl. No.: 15/740,652

(22) PCT Filed: May 10, 2016

(86) PCT No.: PCT/EP2016/060399
§ 371 (c)(1),
(2) Date: Dec. 28, 2017

(87) PCT Pub. No.: WO2017/001097
PCT Pub. Date: Jan. 5, 2017

(65) Prior Publication Data
US 2018/0185015 A1 Jul. 5, 2018

(30) Foreign Application Priority Data
Jun. 29, 2015 (DE) .......................... 10 2015 212 056

(51) Int. Cl.
*A61B 17/02* (2006.01)
*A61B 17/70* (2006.01)
*A61B 17/68* (2006.01)

(52) U.S. Cl.
CPC .......... *A61B 17/025* (2013.01); *A61B 17/708* (2013.01); *A61B 17/7077* (2013.01); *A61B 2017/0256* (2013.01); *A61B 2017/681* (2013.01)

(58) Field of Classification Search
CPC ... A61B 17/02; A61B 17/025; A61B 17/7074; A61B 17/7076; A61B 17/7077; A61B 17/708; A61B 2017/0256; A61B 2017/681
See application file for complete search history.

(56) References Cited

U.S. PATENT DOCUMENTS

| | | | | |
|---|---|---|---|---|
| 4,957,495 A * | 9/1990 | Kluger | ............... | A61B 17/7014 606/258 |
| 10,166,048 B2 * | 1/2019 | Glazer | ............... | A61B 17/7077 |

(Continued)

FOREIGN PATENT DOCUMENTS

| | | |
|---|---|---|
| CN | 202409102 U | 9/2012 |
| DE | 19836498 A1 | 2/2000 |

OTHER PUBLICATIONS

International Search Report and Written Opinion Form PCT/ISA210 and PCT/ISA237, International Application No. PCT/EP2016/060399, p. 1-12, International Filing Date May 10, 2016, mailing date of the search report Jul. 18, 2016.

*Primary Examiner* — Eric S Gibson
(74) *Attorney, Agent, or Firm* — Bond Schoeneck & King, PLLC; George McGuire

(57) ABSTRACT

Disclosed is a device for carrying out a distraction and/or compression of vertebral bodies. The device includes a first and a second extension part with a longitudinal direction, each of which part can be secured on a bone anchor, and having a spreading arrangement for the extension parts, wherein the spreading arrangement has a first receptacle for detachable securing on the first extension part, and the (Continued)

spreading arrangement has at least two arms which form a scissor mechanism, which arms can pivot orthogonally to the longitudinal direction, wherein one end of the first arm is pivotally arranged in the region of the first receptacle and the other end is pivotally connected to the second arm, and the second arm is pivotally connected to a second receptacle which is designed for detachable securing on the second extension part, and the spreading arrangement has a threaded spindle and an inner threaded part which are arranged in such a way that the arms are pivoted with respect to one another when the threaded spindle is screwed in or out in relation to the inner threaded part, the pivoting being such that the receptacles are moved towards each other or away from one another.

11 Claims, 5 Drawing Sheets

(56) References Cited

U.S. PATENT DOCUMENTS

| | | | |
|---|---|---|---|
| 10,335,208 B2* | 7/2019 | Ohnmacht | A61B 17/708 |
| 2005/0203533 A1* | 9/2005 | Ferguson | A61B 17/025 |
| | | | 606/90 |
| 2005/0245928 A1 | 11/2005 | Colleran et al. | |
| 2007/0093828 A1* | 4/2007 | Abdou | A61B 17/025 |
| | | | 606/86 A |
| 2007/0191856 A1* | 8/2007 | Gil | A61B 17/025 |
| | | | 606/90 |
| 2008/0114367 A1 | 5/2008 | Meyer | |
| 2008/0119862 A1* | 5/2008 | Wicker | A61B 17/708 |
| | | | 606/99 |
| 2008/0294206 A1* | 11/2008 | Choi | A61B 17/708 |
| | | | 606/86 A |
| 2010/0024487 A1* | 2/2010 | Khoo | A61B 17/708 |
| | | | 66/90 |
| 2010/0030283 A1* | 2/2010 | King | A61B 17/7037 |
| | | | 606/86 A |
| 2010/0274252 A1* | 10/2010 | Bottomley | A61B 17/708 |
| | | | 606/90 |
| 2013/0110184 A1 | 5/2013 | Wing et al. | |
| 2013/0172947 A1 | 7/2013 | Greenberg | |
| 2013/0289633 A1* | 10/2013 | Gleeson | A61B 17/7074 |
| | | | 606/86 A |
| 2013/0310942 A1* | 11/2013 | Abdou | A61F 2/4455 |
| | | | 623/17.16 |
| 2014/0107656 A1* | 4/2014 | Masson | A61B 17/7077 |
| | | | 606/90 |
| 2014/0249591 A1* | 9/2014 | Peultier | A61B 17/7077 |
| | | | 606/86 A |
| 2015/0066042 A1* | 3/2015 | Cummins | A61B 17/7037 |
| | | | 606/104 |
| 2015/0320458 A1* | 11/2015 | Rezach | A61B 17/7077 |
| | | | 606/279 |
| 2016/0074029 A1* | 3/2016 | O'Connell | A61B 17/0206 |
| | | | 600/213 |
| 2016/0095634 A1* | 4/2016 | Meyer | A61B 17/7077 |
| | | | 606/86 A |
| 2016/0262807 A1* | 9/2016 | Benson | A61B 17/7077 |
| 2017/0042524 A1* | 2/2017 | Angus | A61B 17/025 |
| 2017/0196597 A1* | 7/2017 | Corbin | A61B 17/7049 |
| 2017/0311995 A1* | 11/2017 | Wall | A61B 17/7076 |
| 2018/0185015 A1* | 7/2018 | Heuer | A61B 17/7077 |
| 2018/0185067 A1* | 7/2018 | Ohnmacht | A61B 17/708 |
| 2018/0214189 A1* | 8/2018 | Olea | A61B 17/7001 |
| 2019/0133647 A1* | 5/2019 | Glazer | A61B 17/7077 |

* cited by examiner

DEVICE FOR CARRYING OUT A DISTRACTION FOR A COMPRESSION OF VERTEBRAL BODIES DURING A SPINAL SURGERY

CROSS-REFERENCE TO RELATED APPLICATIONS

This application is the United States National Stage entry under 35 U.S.C. 371 of PCT/EP2016/060399 filed on May 10, 2016, which claims priority to German Application No. 102015212056.2, filed Jun. 29, 2015, the entire disclosure of each of which is incorporated herein by reference.

BACKGROUND OF THE INVENTION

The invention relates to a device for carrying out a distraction and/or compression of vertebral bodies during in particular minimally invasive spinal surgery, said device comprising a first and a second extension part, which parts are in particular sleeve-shaped, at least in portions, and each have a longitudinal direction, and each of which parts can be secured on a bone anchor in a detachable but rigid and rotationally fixed manner, the bone anchors in each case being intended to be inserted or being already inserted into one of the vertebral bodies to be treated, and comprising a spreading arrangement for the extension parts.

In modern spinal surgery, in particular in minimally invasive spinal surgery where sleeve-shaped extension parts of the bone anchors, referred to as extenders, are used, the problem is often that usually adjacent vertebral bodies have to be moved away from one another (distraction) or moved towards one another (compression). The new position can then be fixed by means of osteosynthesis devices, using correction rods. There are instruments for this purpose in the prior art which are sometimes designed in a complex manner and which connect the two extension parts, which parts are rigidly connected to the bone anchors inserted into the vertebral bodies, so as to be adjustable relative to one another. The known devices are complex to produce and complicated to use.

US 2005/024928 A1 discloses a device of the type mentioned at the outset, the spreading arrangement comprising two arms which form a scissor mechanism, a threaded spindle, and an inner threaded part, which are arranged in such a way that the arms are pivoted with respect to one another when the threaded spindle is screwed in or out in relation to the inner threaded part, the pivoting being such that the two extension parts are moved towards each other or away from one another while maintaining their mutual orientation in the plane orthogonal to the longitudinal direction of one extension part.

The object of the present invention is that of developing a device of the type mentioned at the outset, by means of which device, during the distraction or compression, the mutual spacing of the vertebral bodies is changed but the mutual orientation or alignment thereof is not changed or is at least only changed slightly, and which device the surgeon can operate easily and use more flexibly than known devices.

SUMMARY OF THE INVENTION

This object is achieved by a device for carrying out at least one of a distraction and compression of vertebral bodies during spinal surgery.

A spreading arrangement designed in this way can be used to perform a distraction or a compression of vertebral bodies such that the mutual orientation of said vertebral bodies is substantially maintained. This is achieved by the spreading arrangement changing the spacing between the two extension parts uniformly over the extension thereof when the threaded spindle is screwed in or out, without at the same time pivoting the extension parts with respect to one another. This is achieved according to the invention in that, in the claimed device, the pivot axes of the arms of the spreading arrangement and/or of the scissor mechanism extend in parallel with the longitudinal direction of the first extension part.

In a development of the invention, it is proposed for the second receptacle to comprise a spherically mounted insert that can be fixed, in particular clamped, against the second extension part such that the second extension part can be secured in the second receptacle while maintaining its orientation relative to the first extension part. This makes it possible for extension parts that are angled obliquely relative to one another to also be fixed in the spreading arrangement without torques being applied to the extension parts in the process, which torques substantially change the orientation of said extension parts. The spherically mounted insert thus quasi adapts to the orientation of the second extension part. In this state, the second receptacle is then fixed against the second extension part.

In a further concept of the invention, it is proposed for the first receptacle and/or the second receptacle to be sleeve-shaped and to be able to be pushed or placed onto the extension part in the longitudinal direction and to be able to be detachably fixed, in particular clamped, in the pushed-on or placed-on state. This embodiment is advantageous because, in such cases, the device can be attached to the extension parts in a usage position intended by the surgeon in a simple, quick and safe manner during the operation.

In a development of this concept of the invention, it is advantageous for the first receptacle and/or the second receptacle to comprise a slotted sleeve. Specifically, this makes it possible to adapt the inner diameter of the slotted sleeve, in the state when not pushed on, to the outer diameter of the associated extension part, such that the spreading arrangement can be pushed onto the associated extension parts and can either be clamped in an intended position or can be fixed by additional clamping means.

In a development of the last-mentioned concept, it is further proposed for the inner circumferential length of the slotted sleeve to be able to be varied by an adjustment means, in particular a screw, such that the slotted sleeve can be clamped against the outer circumference of the associated extension part. The inner circumferential length of the slotted sleeve could thus be varied and fixed in the manner of a hose clamp.

In a development of the invention, it is proposed for an additional, identically acting arm to be provided in each case in parallel with the first and with the second arm. This increases the stability of the spreading arrangement.

Another or additional stabilization can advantageously be achieved in that the spreading arrangement comprises two additional arms which, together with the first and the second arm, form a parallelogram-shaped scissor mechanism and are pivotally connected in a corresponding manner to the first and the second receptacle and to one another. Additional identically acting arms, which are in each case parallel and mutually spaced in particular by means of spacer sleeves, could also be provided in each case in the region of the two additional arms. In the case of a parallelogram-shaped scissor mechanism, it is advantageous for the inner threaded part to be pivotally mounted in the region of the two additional arms.

It is also advantageous for the threaded spindle to be rotatably mounted and axially supported with respect to the longitudinal direction thereof in the region of the pivotable connection of the first and the second arm.

The threaded spindle comprises an actuating head that can be accessed and grasped by hand, so that said spindle can be rotated by hand, i.e. without requiring tools, in order to perform the distraction or compression. However, alternatively or in addition, the threaded spindle can also comprise a tool application point.

The extension parts can have a discrete or preferred position for fixing the spreading arrangement. It is advantageous, however, for the spreading arrangement to be able to be positioned and detachably fixed relative to the first and second extension part in a position that is variable in the longitudinal direction of said parts.

Further features, details and advantages of the invention can be found in the accompanying claims and in the schematic drawings and the following description of a preferred embodiment of the invention.

DETAILED DESCRIPTION

Figure 1B:
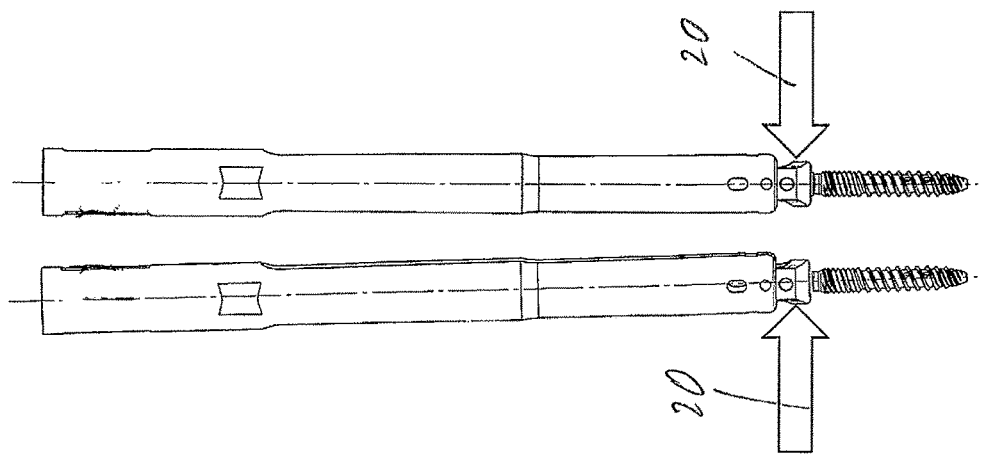
FIG. 1b is a schematic view of the known conditions during a compression of vertebral bodies during spinal surgery.
Figure 1A:
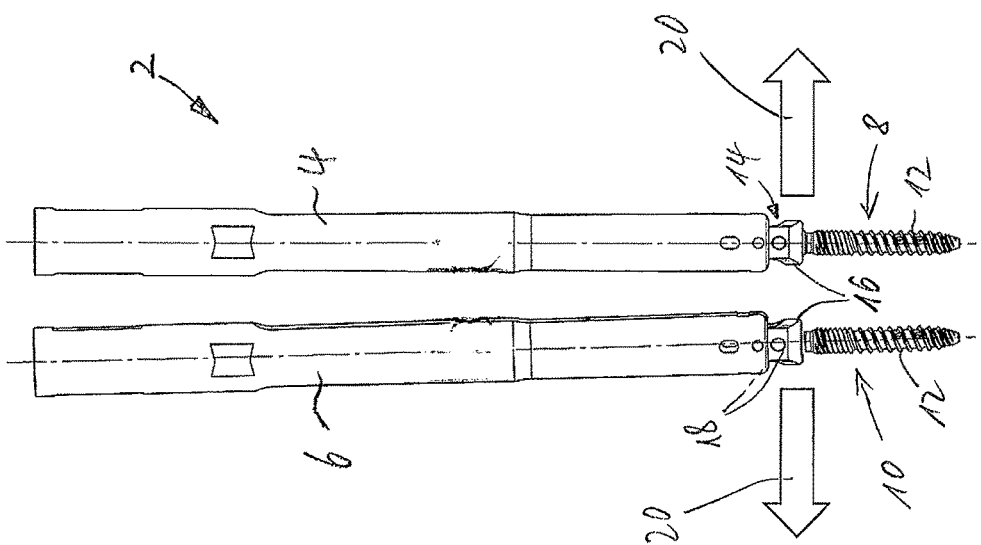
FIG. 1a is a schematic view of the known conditions during a distraction of vertebral bodies during spinal surgery.

FIG. 1a schematically shows the conditions during a distraction and FIG. 1b shows said conditions during a compression of vertebral bodies during spinal surgery. A device denoted overall by reference sign 2 is shown schematically, said device comprising a first and a second sleeve-shaped extension part 4 and 6, respectively, shown by way of example in an upper region. Each extension part 4, 6 is connected to an associated bone anchor 8 and 10, respectively, in a detachable but rigid and rotationally fixed manner. The bone anchor 8, 10 is, by way of example and preferably, an osteosynthesis device, the bone anchor 8, 10 in each case comprising a threaded shank 12 to be screwed into a vertebral body, and a clevis 16 that is U-shaped in a side view, comprises a receiving opening 14 for a correction element, in particular a correction rod, and comprises two legs 18. In this case, the relevant screw shank 12 is either formed rigidly, in particular integrally, with the clevis 16, or in each case comprises a head that is pivotally mounted inside the clevis 16 and is permanently secured by the surgeon in an intended pivot position relative to the clevis 16. The latter case is referred to as a polyaxial bone anchor, in particular a polyaxial bone screw. After the bone anchors 8, 10 have been inserted, in particular screwed, into usually adjacent vertebral bodies, a distraction (FIG. 1a) or a compression (FIG. 1b) of the vertebral bodies relative to one another can be performed by means of forces being exerted by the extension parts 4, 6 on the bone anchors 8, 10 that are screwed into the vertebral bodies. This is indicated by arrows 20 in each case.

Figure 2:
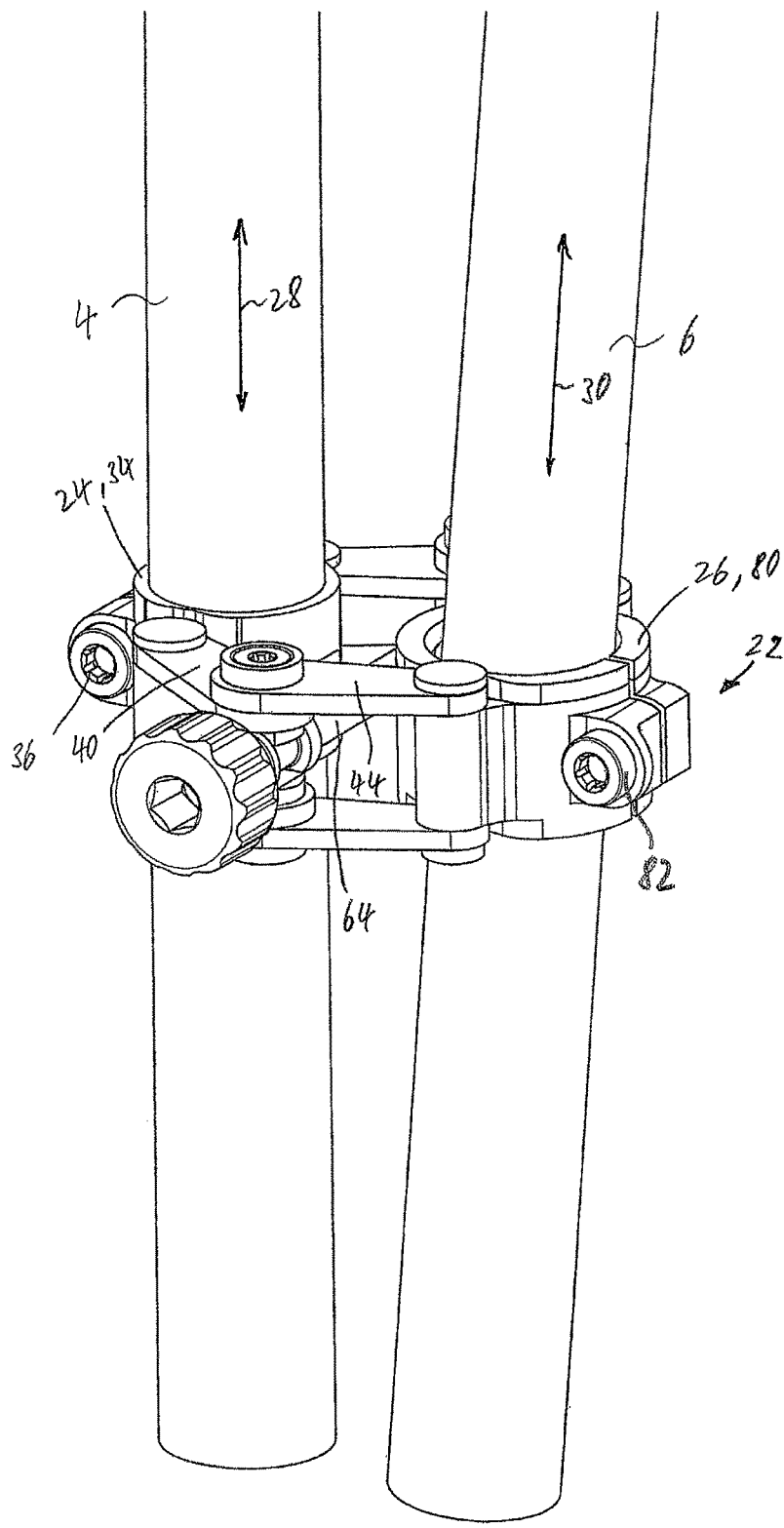
FIG. 2 is a perspective view of a device according to the invention for carrying out a distraction and/or a compression of vertebral bodies during spinal surgery, comprising two extension parts and a spreading arrangement that are shown only schematically.

FIG. 2 shows a device 2 according to the invention, comprising a first and a second extension part 4, 6, which are in particular sleeve-shaped, at least in portions, and a spreading arrangement 22. The spreading arrangement 22 comprises a scissor mechanism consisting of hingedly interconnected arms that are arranged in the shape of a parallelogram, which mechanism will be described in detail in the following.

Figure 3:
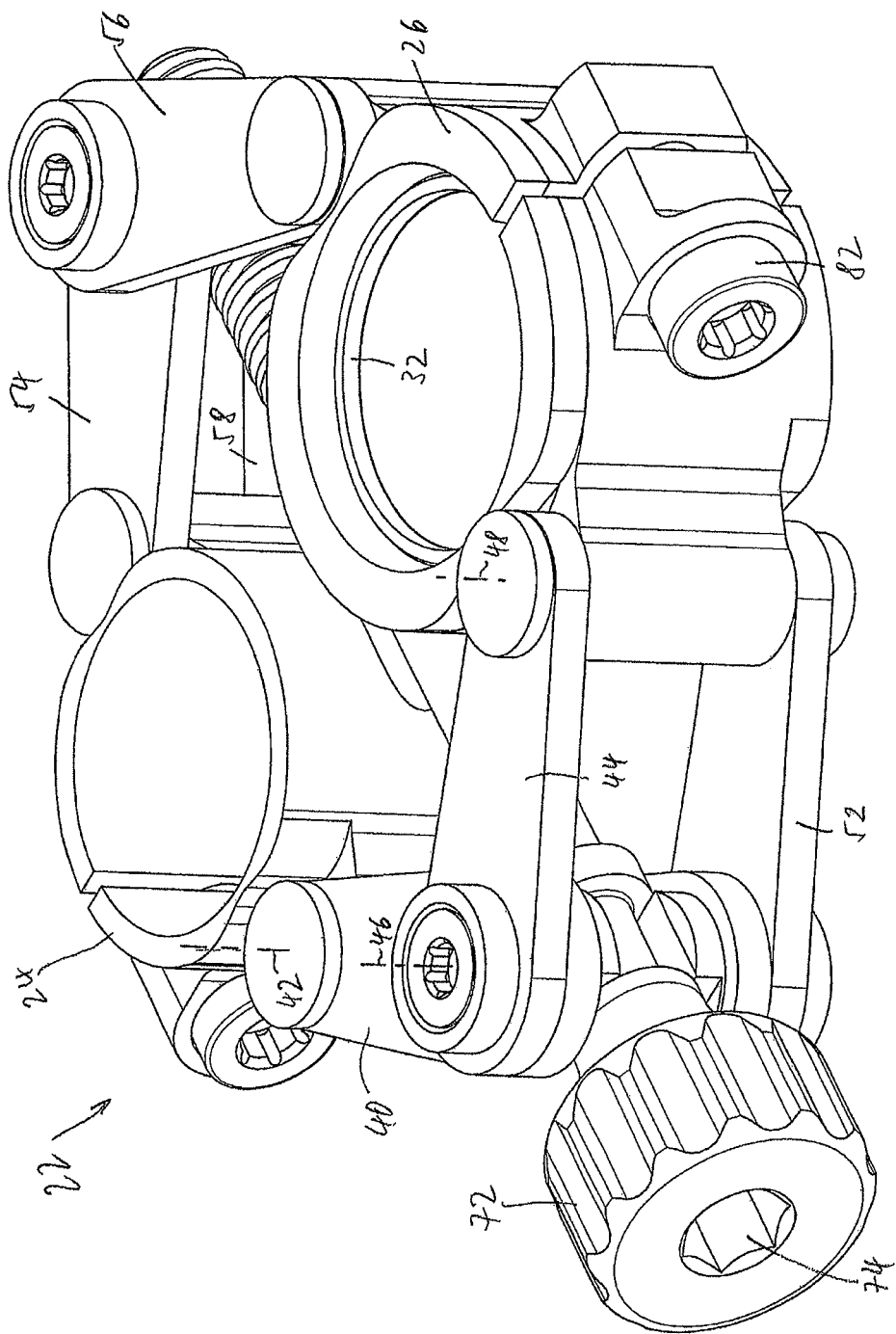
FIG. 3 is a perspective view of the spreading arrangement according to FIG. 2.
Figure 4:
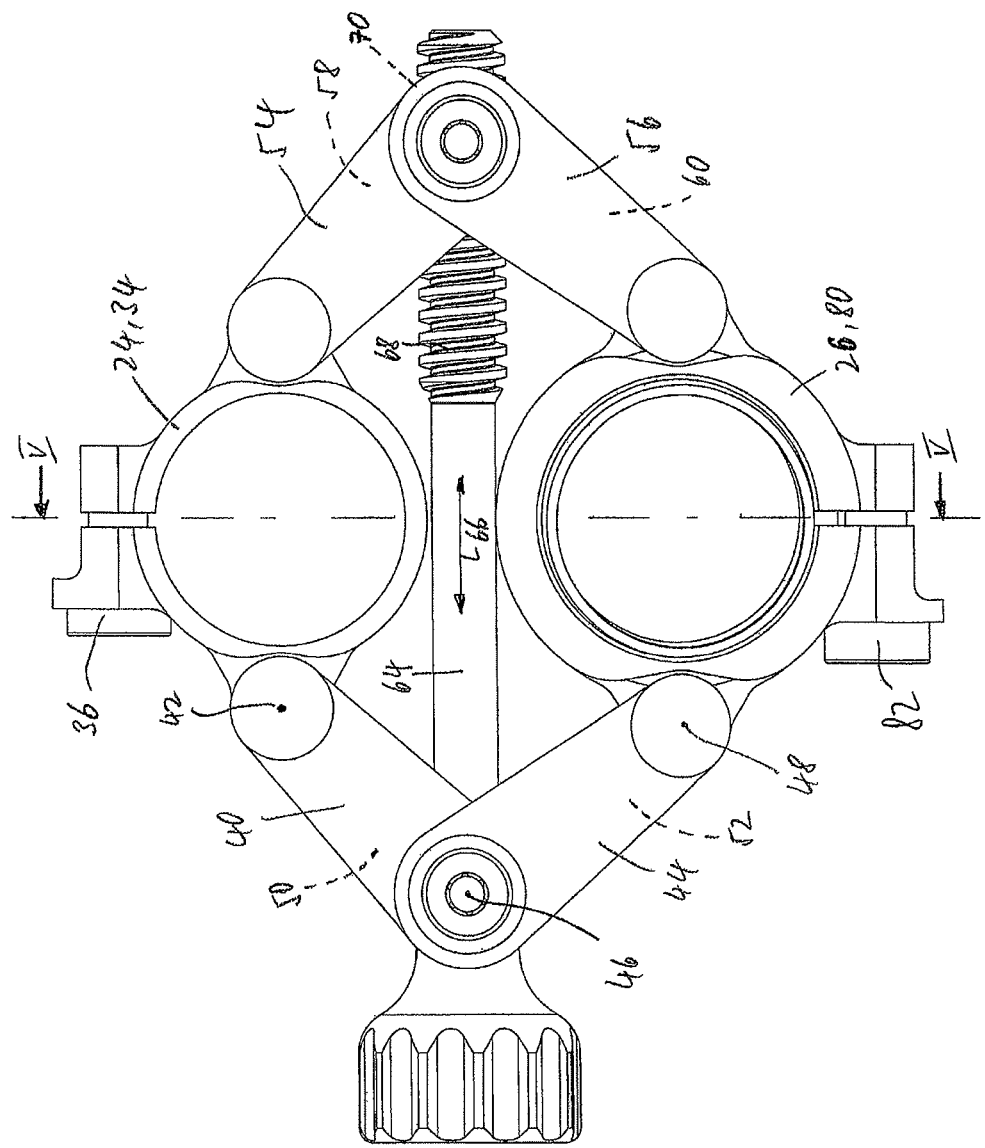
FIG. 4 is a plan view of the spreading arrangement according to FIG. 3.
Figure 5:
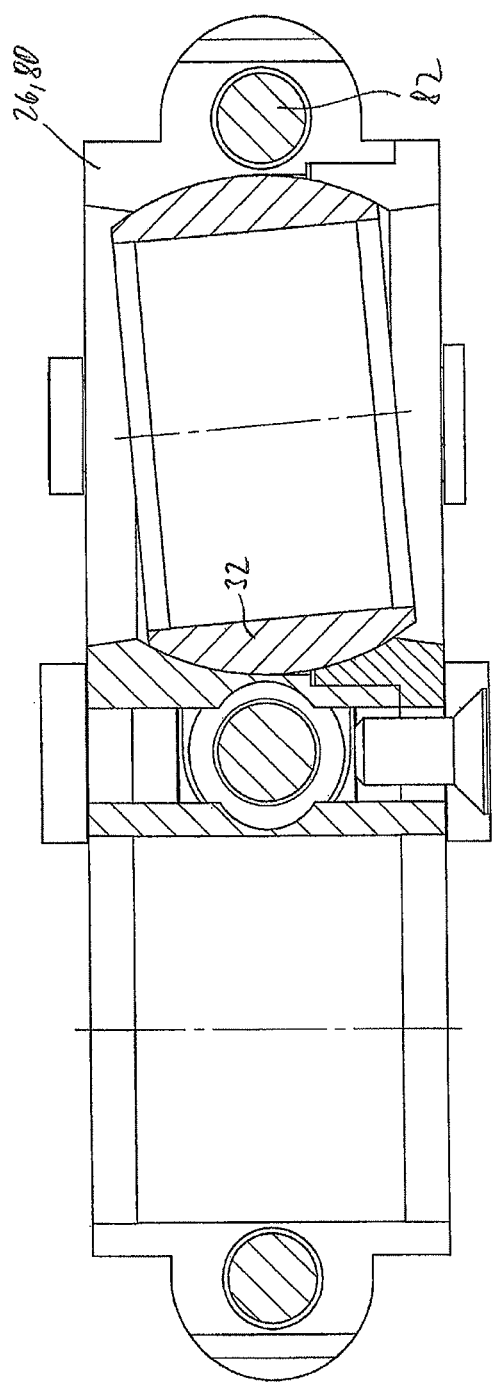
FIG. 5 is a partly sectional view of the spreading arrangement according to FIG. 4, in the cutting plane V-V.

The spreading arrangement 22 further comprises a first receptacle 24 for detachably securing the spreading arrangement 22 on the first extension part 4, and a second receptacle 26 for detachably securing the spreading arrangement 22 on the second extension part 6. As shown schematically in FIG. 2, the extension parts 4 and 6 are not exactly parallel but instead are angled obliquely relative to one another. The longitudinal directions 28 and 30 thereof are indicated and quasi form the extension of the longitudinal direction of the relevant clevis 16 of the bone anchor 8 and/or 10. In order to adapt this, the spreading arrangement 22 or the second receptacle 26 thereof comprises a spherically mounted insert 32 that can be seen in the sectional view of FIG. 5 but also in FIGS. 3 and 4. The spherically mounted insert 32 can be pivoted in the spreading arrangement 22 so as to be able to adapt an alignment of the longitudinal direction 30 of the second extension part 6 that is not orthogonal relative to a pivot plane of the scissor mechanism and/or of the spreading arrangement 22.

The first receptacle 24 comprises, by way of example, a slotted sleeve 34 which can be detachably fixed, in the manner of a hose clamp, around the outer circumference of the first extension part 4, using a screw 36 as an adjustment means. In this way, the pivot plane of the spreading arrangement is fixed orthogonally to the longitudinal direction 28 of the first extension part 4. The spreading arrangement 22 comprises a first arm 40, one end of which is pivotally hinged in the region of the first receptacle 24 so as to be pivotable about an axis that is parallel to the longitudinal direction 28. The other end of the first arm 40 is connected to a second arm 44 so as to be pivotable about an axis 46 that is parallel to the axis 42. The other end of the second arm 44 is in turn pivotally hinged to the second receptacle 26 so as to be pivotable about an axis 48 that is parallel to the axis 46. All the pivot axes thus extend in parallel with the longitudinal direction 28 of the first extension part 4.

It can be seen from the perspective views that a further identically operating arm 50 and 52 is provided in each case in parallel with the first and second arm 40, 44 so as to be pivotable about the corresponding axes. This increases the torsion-resistance of the spreading arrangement 22. Furthermore, the torsion-resistance of the spreading arrangement is increased by the spreading arrangement comprising two further arms 54 and 56 that are opposite the first and the second arm 40 and 44, respectively, in the drawing plane in FIG. 4, and that are pivotally connected to one another and to the first and second receptacle 24, 26 by means of corresponding identically acting axes, such that a parallelogram-shaped scissor mechanism is formed. In turn, arms 58 and 60 are provided accordingly in parallel with the two additional arms 54, 56. The scissor mechanism is thus quasi mirror-symmetrical in two planes that are mutually spaced in the longitudinal direction 28.

The spreading arrangement 22 further comprises a threaded spindle 64, the longitudinal direction 66 of which is in the pivot plane of the spreading arrangement 22, i.e. orthogonal to the longitudinal direction 28 of the first extension part 4. The threaded spindle 64 comprises an outer threaded portion 68 that can be screwed into an inner threaded part 70 that is pivotally mounted in the region of the two additional arms 54, 56.

The other end of the threaded spindle 64 is rotatably mounted and axially supported with respect to the longitudinal direction 66 thereof in the region of the pivotable connection of the first and second arm 40, 44. This can be achieved for example by means of a radially outwardly projecting annular collar of the threaded spindle 64. The threaded spindle 64 further comprises an actuating head 72 that can be grasped by hand, a tool attachment point 74 also being provided for rotating the actuating head 72.

The second receptacle 26 also comprises a slotted sleeve 80 and an adjustment screw 82. Tightening the adjustment screw 82 reduces the inner circumference of the slotted sleeve 80, such that the spherically mounted insert 32 is immovably arranged relative to the second receptacle 26 and is fixed against the second extension part 6.

If the two receptacles 24, 26 are positionally fixed relative to the first and second extension part 4 and 6, respectively, the receptacles 24, 26 are moved away from one another (distraction) or towards each other (compression) when the threaded spindle 64 is screwed in or out in relation to the inner threaded part 70. This adjustment movement occurs in the pivot plane of the scissor mechanism and/or of the spreading arrangement 22, i.e. exactly orthogonally to the longitudinal direction 28 of the first extension part 4. The relative mutual orientation of the extension parts 4, 6, and thus also of the bone anchors 8, 10 and the associated vertebral bodies in which the bone anchors 8, 10 are inserted, is therefore maintained, or at least only slightly changed, during the distraction or compression.

What is claimed is:

1. A device for carrying out at least one of a distraction and compression of vertebral bodies during in particular minimally invasive spinal surgery, said device comprising: a first and a second extension part, which parts are sleeve-shaped, at least in portions, and each have a longitudinal direction, and each of which parts can be secured on a bone anchor in a detachable but rigid and rotationally fixed manner, the bone anchors in each case being either of adapted for insertion or being already inserted into one of the vertebral bodies to be treated, and comprising a spreading arrangement for the extension parts, wherein the spreading arrangement has a first receptacle for detachably securing the spreading arrangement on the first extension part, wherein the spreading arrangement has at least two arms which form a scissor mechanism, which arms can pivot in a plane orthogonal to the longitudinal direction of the first extension part, wherein one end of a first arm is pivotally arranged in a region of the first receptacle and another end is pivotally connected to a second arm, and wherein said second arm is pivotally connected, remote from the first arm, to a second receptacle which is adapted for detachable securing on the second extension part, and wherein the spreading arrangement has a threaded spindle and an inner threaded part which are arranged in such a way that the arms are pivoted with respect to one another when the threaded spindle is screwed in or out in relation to the inner threaded part, the pivoting being such that the receptacles, and thus the extension parts are moved towards each other or away from one another while maintaining a mutual orientation in the plane orthogonal to the longitudinal direction of the first extension part.

2. Device according to claim 1, characterized in that the second receptacle comprises a spherically mounted insert that can be fixed against the second extension part such that the second extension part can be secured in the second receptacle while maintaining its orientation relative to the first extension part.

3. Device according to claim 1, characterized in that at least one of the first receptacle and/or the second receptacle is sleeve-shaped and can be placed onto the extension part in the longitudinal direction and can be detachably fixed in the placed-on state.

4. Device according to claim 1, characterized in that at least one of the first receptacle and the second receptacle comprise a slotted sleeve.

5. Device according to claim 4, characterized in that an inner circumferential length of the slotted sleeve can be varied by an adjustment means, such that the slotted sleeve can be clamped against an outer circumference of a associated extension part.

6. Device according to claim 1, characterized in that an additional, identically acting arm is provided in each case in parallel with the first arm and with the second arm.

7. Device according to claim 1, characterized in that the spreading arrangement comprises two additional arms which, together with the first and the second arm, form a parallelogram-shaped scissor mechanism and are pivotally connected in a corresponding manner to the first and the second receptacles and to one another.

8. Device according to claim 7, characterized in that the inner threaded part is pivotally mounted in a region of the two additional arms.

9. Device according to claim 1, characterized in that the threaded spindle is rotatably mounted and axially supported with respect to the longitudinal direction thereof in a region of the pivotable connection of the first arm and the second arm.

10. Device according to claim 1, characterized in that the threaded spindle comprises an actuating head that can be accessed and grasped by hand.

11. Device according to claim 1, characterized in that the spreading arrangement can be positioned and detachably fixed relative to the first and second extension part in a position that is variable in the longitudinal direction of said parts.

* * * * *

UNITED STATES PATENT AND TRADEMARK OFFICE
CERTIFICATE OF CORRECTION

PATENT NO. : 10,441,263 B2
APPLICATION NO. : 15/740652
DATED : October 15, 2019
INVENTOR(S) : Frank Heuer and Timo Ohnmacht Page 1 of 1

It is certified that error appears in the above-identified patent and that said Letters Patent is hereby corrected as shown below:

On the Title Page

Item (54) and in the Specification, Column 1, Lines 1-4, correct the title from:
DEVICE FOR CARRYING OUT A DISTRACTION FOR A COMPRESSION OF VERTEBRAL BODIES DURING A SPINAL SURGERY
To:
DEVICE FOR CARRYING OUT A DISTRACTION OR A COMPRESSION OF VERTEBRAL BODIES DURING A SPINAL SURGERY Signed and Sealed this
Ninth Day of March, 2021

Drew Hirshfeld
*Performing the Functions and Duties of the
Under Secretary of Commerce for Intellectual Property and
Director of the United States Patent and Trademark Office*